US010436727B2

(12) United States Patent
Valori et al.

(10) Patent No.: US 10,436,727 B2
(45) Date of Patent: Oct. 8, 2019

(54) PREDICTION OF GAS PRODUCTION RATES FROM TIME-DEPENDENT NMR MEASUREMENTS

(71) Applicant: Schlumberger Technology Corporation, Sugar Land, TX (US)

(72) Inventors: Andrea Valori, Dhahran (SA); Reza Taherian, Missouri City, TX (US); Farhan Ali, Dammam (SA); Wael Abdallah, Dhahran (SA); Mohammed Badri, Al-Khobar (SA); Richard Lewis, Longmont, CO (US)

(73) Assignee: SCHLUMBERGER TECHNOLOGY CORPORATION, Sugar Land, TX (US)

( * ) Notice: Subject to any disclaimer, the term of this patent is extended or adjusted under 35 U.S.C. 154(b) by 468 days.

(21) Appl. No.: 15/153,924

(22) Filed: May 13, 2016

(65) Prior Publication Data

US 2016/0334347 A1 Nov. 17, 2016

Related U.S. Application Data

(60) Provisional application No. 62/162,276, filed on May 15, 2015.

(51) Int. Cl.
  *G01N 24/08* (2006.01)
  *G01R 33/44* (2006.01)
(52) U.S. Cl.
  CPC ......... *G01N 24/081* (2013.01); *G01R 33/448* (2013.01)

(58) Field of Classification Search
  CPC .................. G01N 24/081; G01R 33/448
  See application file for complete search history.

(56) References Cited

U.S. PATENT DOCUMENTS

| 7,893,692 B2 * | 2/2011 | Minh | G01V 3/32 |
| | | | 324/303 |
| 2011/0068798 A1 * | 3/2011 | Minerbo | G01V 3/28 |
| | | | 324/343 |

(Continued)

OTHER PUBLICATIONS

Gombia, M. et al., "Nanopore Structure Buildup during Endodontic Cement Hydration Studied by Time-Domain Nuclear Magnetic Resonance of Lower and Higher Mobility 1H", Journal of Physical Chemistry B, 2010, 114(5), pp. 1767-1774.

(Continued)

*Primary Examiner* — Farhana A Hoque

(57) ABSTRACT

A tool having a pump-out unit, pumping unit, and NMR unit is disposed in a wellbore. On a pump-up cycle, after removing borehole fluids, a fluid is injected into a region of investigation. NMR measurements are made while fluid migrates into the region of investigation. On a production cycle, pressure is removed, allowing fluid to exit the formation while NMR measurements are made. A rate of fluid production is estimated using the time-dependent NMR measurements. Alternatively, the mass of a sample is measured. Fluid is injected into the sample and the mass of the injected sample is measured. Pressure is removed and the mass of the injected sample as the fluid migrates out of the sample is measured. The change in mass of the injected sample as the fluid migrates out of the sample is determined and a rate of fluid production is estimated using the determined change in mass.

23 Claims, 10 Drawing Sheets

(56) References Cited

U.S. PATENT DOCUMENTS

2011/0234220 A1* 9/2011 Mitchell ............. G01N 24/081
324/303
2011/0274994 A1* 11/2011 Carrier ..................... C01B 3/22
429/419
2016/0178786 A1 6/2016 Badri et al.

OTHER PUBLICATIONS

Bohris, A. J. et al., "A Broad Line NMR and MRI Study of Water and Water Transport in Portland Cement Pastes", Magnetic Resonance Imaging, 1998, 16(5-6), pp. 455-461.
Van Landeghem, M. et al., "The Roles of Hydration and Evaporation During the Drying of a Cement Paste by Localized NMR", Cement and Concrete Research, 2013, 48, pp. 86-96.
Sigal, R. F. et al., "Laboratory NMR Measurements on Methane Saturated Barnett Shale Samples", Petrophysics, 2011, 52(1), pp. 32-49.
Gentiletti, L. B., "Nuclear Magnetic Resonance as a Tool for On-Line Catalytic Reaction Monitoring" (Mar. 2010), 133 pp.
Oligschlager, D. et al., "Miniature Mobile NMR Sensors for Material Testing and Moisture-Monitoring", The Open-Access Journal for the Basic Principles of Diffusion Theory, (2014) 25 pp.
Fleury, M., "Characterization of Shales With Low Field NMR", SCA2014-014, Society of Core Analysts, Sep. 2014, 12 pp.
Kausik, R. et al, "Characterization of Gas Dynamics in Kerogen Nanopores by NMR", SPE 147198, Society of Petroleum Engineers (2011) 16 pp.

* cited by examiner

PREDICTION OF GAS PRODUCTION RATES FROM TIME-DEPENDENT NMR MEASUREMENTS

CROSS REFERENCE TO RELATED APPLICATIONS

This application claims priority from U.S. Ser. No. 62/162,276, filed May 15, 2015, the contents of which are incorporated herein by reference.

BACKGROUND

Time-dependent nuclear magnetic resonance (NMR) has been used to monitor chemical reactions, for example, in the cement and paint industries. Parameters such as humidity monitoring, hydration, and evaporation in cement during the drying of a cement paste have been studied using NMR. The decomposition of aqueous hydrogen peroxide solutions has also been studied in detail, and NMR has also been used as an online reaction monitoring tool and for material testing and moisture monitoring. Natural gas (i.e., methane) in shale samples has been studied with both $T_2$ and $T_1$-$T_2$ experiments, and also as a function of pressure. These various applications and studies suggest that NMR logging measurements can provide quantitative estimates of the free gas storage and the percentage of free gas stored in organic pores. However, the time-dependence of the saturation and de-saturation phenomena has not been investigated and incorporated into such estimates, and such information can be useful in determining potential gas production rates.

SUMMARY

This summary is provided to introduce a selection of concepts that are further described below in the detailed description. This summary is not intended to identify key or essential features of the claimed subject matter, nor is it intended to be used as an aid in limiting the scope of the claimed subject matter.

A tool having a pump-out unit, pumping unit, and NMR unit is disposed in a wellbore. On a pump-up cycle, after removing borehole fluids, a fluid is injected into a region of investigation. NMR measurements are made while fluid migrates into the region of investigation. On a production cycle, pressure is removed, allowing fluid to exit the formation while NMR measurements are made. A rate of fluid production is estimated using the time-dependent NMR measurements. Alternatively, the mass of a sample is measured. Fluid is injected into the sample and the mass of the injected sample is measured. Pressure is removed and the mass of the injected sample as the fluid migrates out of the sample is measured. The change in mass of the injected sample as the fluid migrates out of the sample is determined and a rate of fluid production is estimated using the determined change in mass.

BRIEF DESCRIPTION OF THE DRAWINGS

The present disclosure is best understood from the following detailed description when read with the accompanying figures. It is emphasized that, in accordance with the standard practice in the industry, various features are not drawn to scale. In fact, the dimensions of the various features may be arbitrarily increased or reduced for clarity of discussion. Embodiments are described with reference to the following figures. The same numbers are generally used throughout the figures to reference like features and components.

DETAILED DESCRIPTION

Figure 1A:
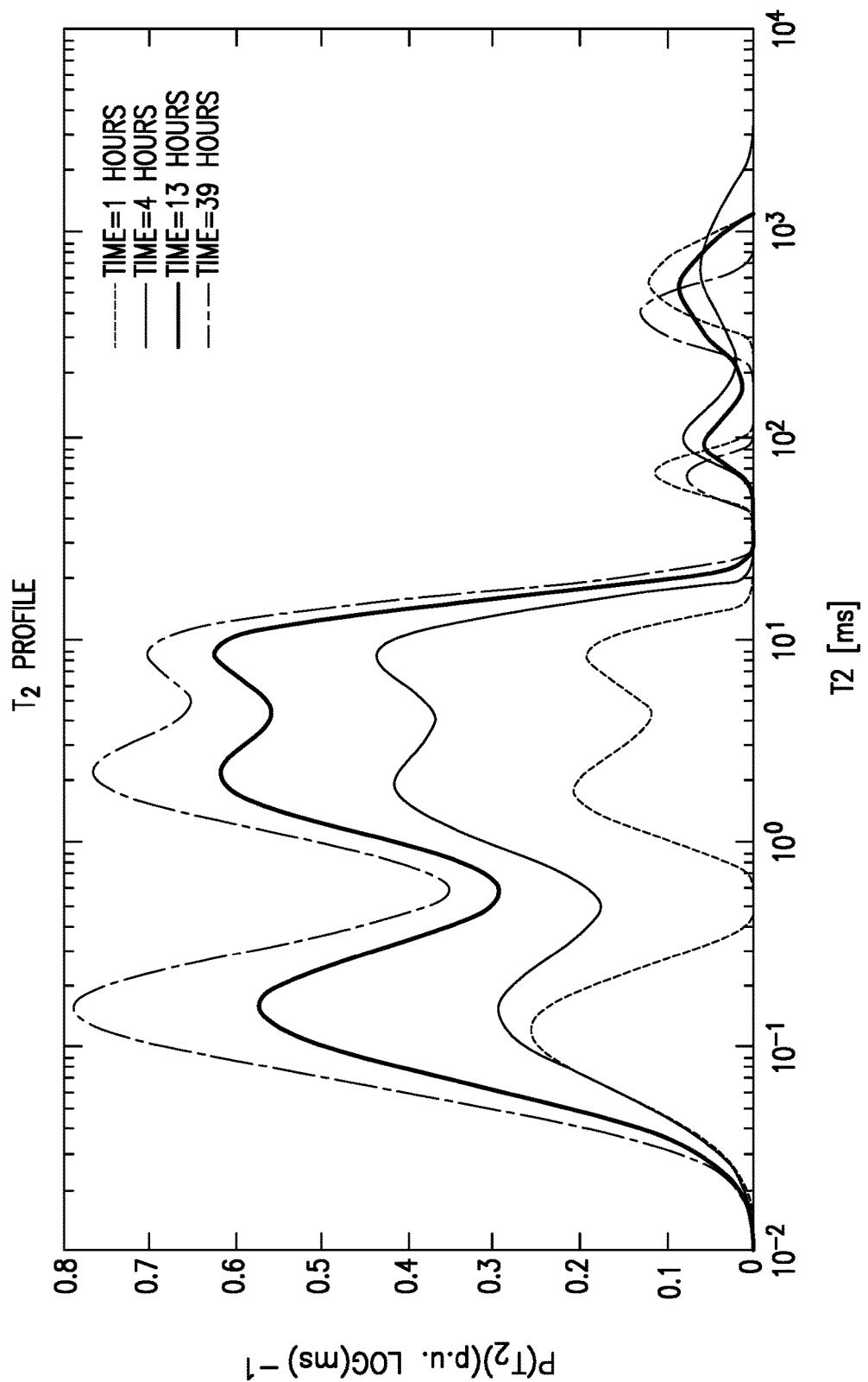
FIG. 1A is a plot showing a series of $T_2$ distributions acquired on a shale sample as a function of increasing time while injecting methane gas at a constant pressure, in accordance with the present disclosure.

It is to be understood that the following disclosure provides many different embodiments, or examples, for implementing different features of various embodiments. Specific examples of components and arrangements are described below to simplify the present disclosure. These are, of course, merely examples and are not intended to be limiting. In addition, the present disclosure may repeat reference numerals and/or letters in the various examples. This repetition is for the purpose of simplicity and clarity and does not in itself dictate a relationship between the various embodiments and/or configurations discussed. Moreover, the formation of a first feature over or on a second feature in the description that follows may include embodiments in which the first and second features are formed in direct contact, and may also include embodiments in which additional features may be formed interposing the first and second features, such that the first and second features may not be in direct contact.

Some embodiments will now be described with reference to the figures. Like elements in the various figures may be referenced with like numbers for consistency. In the following description, numerous details are set forth to provide an understanding of various embodiments and/or features. However, it will be understood by those skilled in the art that some embodiments may be practiced without many of these details and that numerous variations or modifications from the described embodiments are possible. As used here, the terms "above" and "below", "up" and "down", "upper" and "lower", "upwardly" and "downwardly", and other like terms indicating relative positions above or below a given point or element are used in this description to more clearly describe certain embodiments. However, when applied to equipment and methods for use in wells that are deviated or horizontal, such terms may refer to a left to right, right to left, or diagonal relationship, as appropriate. It will also be understood that, although the terms first, second, etc. may be used herein to describe various elements, these elements should not be limited by these terms. These terms are only used to distinguish one element from another.

The terminology used in the description herein is for the purpose of describing particular embodiments only and is not intended to be limiting. As used in the description and the appended claims, the singular forms "a", "an" and "the" are intended to include the plural forms as well, unless the context clearly indicates otherwise. It will also be understood that the term "and/or" as used herein refers to and encompasses any and all possible combinations of one or more of the associated listed items. It will be further understood that the terms "includes," "including," "comprises," and/or "comprising," when used in this specification, specify the presence of stated features, integers, steps, operations, elements, and/or components, but do not preclude the presence or addition of one or more other features, integers, steps, operations, elements, components, and/or groups thereof.

As used herein, the term "if" may be construed to mean "when" or "upon" or "in response to determining" or "in response to detecting," depending on the context. Similarly, the phrase "if it is determined" or "if [a stated condition or event] is detected" may be construed to mean "upon determining" or "in response to determining" or "upon detecting [the stated condition or event]" or "in response to detecting [the stated condition or event]," depending on the context.

A system and method to use time-dependent NMR measurements to determine fluid production rates from different geologic reservoirs is disclosed. In at least one embodiment, gas is injected into a sample under pressure until the sample is saturated with the gas. The pressure is removed after saturation. An NMR signal is measured while the gas migrates into or out of the sample. Thus, the prediction of a fluid production rate from a porous reservoir can be made by performing time dependent NMR measurements downhole or mimicking a production well through laboratory NMR measurements on rock samples. Relative contributions from different pore systems or pore fluids can be discerned based on $T_2$ distributions (or other NMR parameters). Multi-component decay for a single $T_2$ value may be interpreted as representing the effects of production from pores/pore throats of different sizes or pore fluids in different states. Alternatively, at least in the laboratory, after the sample is saturated, the weight of the sample may be measured while the gas migrates out of the sample, and those measurements may be used to determine fluid production rates.

In at least one embodiment a shale sample is placed in an atmosphere of proton-bearing gas. Methane may be used as such a saturating gas since it has a high hydrogen index and is similar to what is found in many gas reservoirs. While the data discussed herein refer to methane gas (for ease of discussion), the techniques disclosed herein can be used to detect other hydrocarbons or proton-bearing substances (whether gaseous, liquid, or supercritical). In addition, target elements such as carbon, oxygen, or sodium may be modified so that non-proton-bearing substances can be detected. Thus, while proton ($^1$H) NMR may be the most natural, economic, and straightforward type of NMR, in principle this technique can be applied to different spin-bearing elements such as $^{13}$C, $^2$H, $^6$Li, $^{10}$B, $^{11}$B, $^{14}$N, $^{15}$N, $^{17}$O, $^{19}$F, $^{23}$Na, $^{29}$Si, $^{31}$P, $^{35}$Cl, $^{113}$Cd, $^{129}$Xe $^{195}$Pt.

In addition, techniques disclosed herein are not limited to shale, but can be applied to other permeable, porous media. An independent variable (such as pressure) can be applied in a single step (e.g., to the maximum pressure used) from the beginning of the experiment, or the independent variable can be incrementally changed to study the dependence of various phenomena as a function of the independent variable.

In an embodiment in which a sample is exposed to higher pressure, several NMR measurements are performed at known times as gas enters the sample. One class or type of NMR measurements provides a $T_2$ distribution. This is a reasonably fast measurement and therefore allows capturing variations on short timescales. Other possible NMR measurement types include $T_1$-$T_2$ distributions and diffusion distributions. Measurements can be made at fixed or varied intervals of time. For example, the measurements can be kept closely spaced in time at the beginning of the saturation process to capture the faster variation just after the gas pressure is applied. Further measurements, more spaced in time, can be obtained to decrease the overall data amount or increase the signal to noise averaging for longer times.

When the sample is saturated with gas, the gas pressure is removed and the gas is allowed to migrate from the sample. The decay of the signal is monitored similar to the manner in which it was monitored during the increase of signal (i.e., during the pressurization/saturation phase). Full saturation (or equilibrium with the applied gas atmosphere) may be used to improve SNR (signal to noise ratio); however, removal of the applied pressure can also be done at some intermediate saturation level. Pressure can be removed completely in a single step (as mentioned for the pressure increase) or decreased incrementally.

NMR-compatible core holders are typically specialized equipment that are expensive, complicated to use, and limited to (relatively) low-pressure ratings. Often they have considerable background NMR signal that should be removed from the NMR data during the data processing stage. However, the techniques described herein do not require the pressure vessel be compatible with simultaneous NMR acquisition. For example, the sample can be saturated in a pressure vessel kept outside the NMR equipment and then transferred to the NMR equipment for the de-saturation monitoring.

FIG. 1A shows a series of $T_2$ distributions acquired on a shale sample (Sample 1) as a function of increasing time while injecting methane gas at a constant pressure. Since the signal of the sample itself has been removed from the data, the remaining signal relates to the signature of the methane gas as a function of time. The figure shows that as injection time increases more methane gas enters the sample pore system and passes into different NMR "regions". This may be due, for example, to the movement of the gas to pores of different sizes or from a transformation of the gas to a different state (e.g., absorbed phase vs. free gas).

Figure 1B:
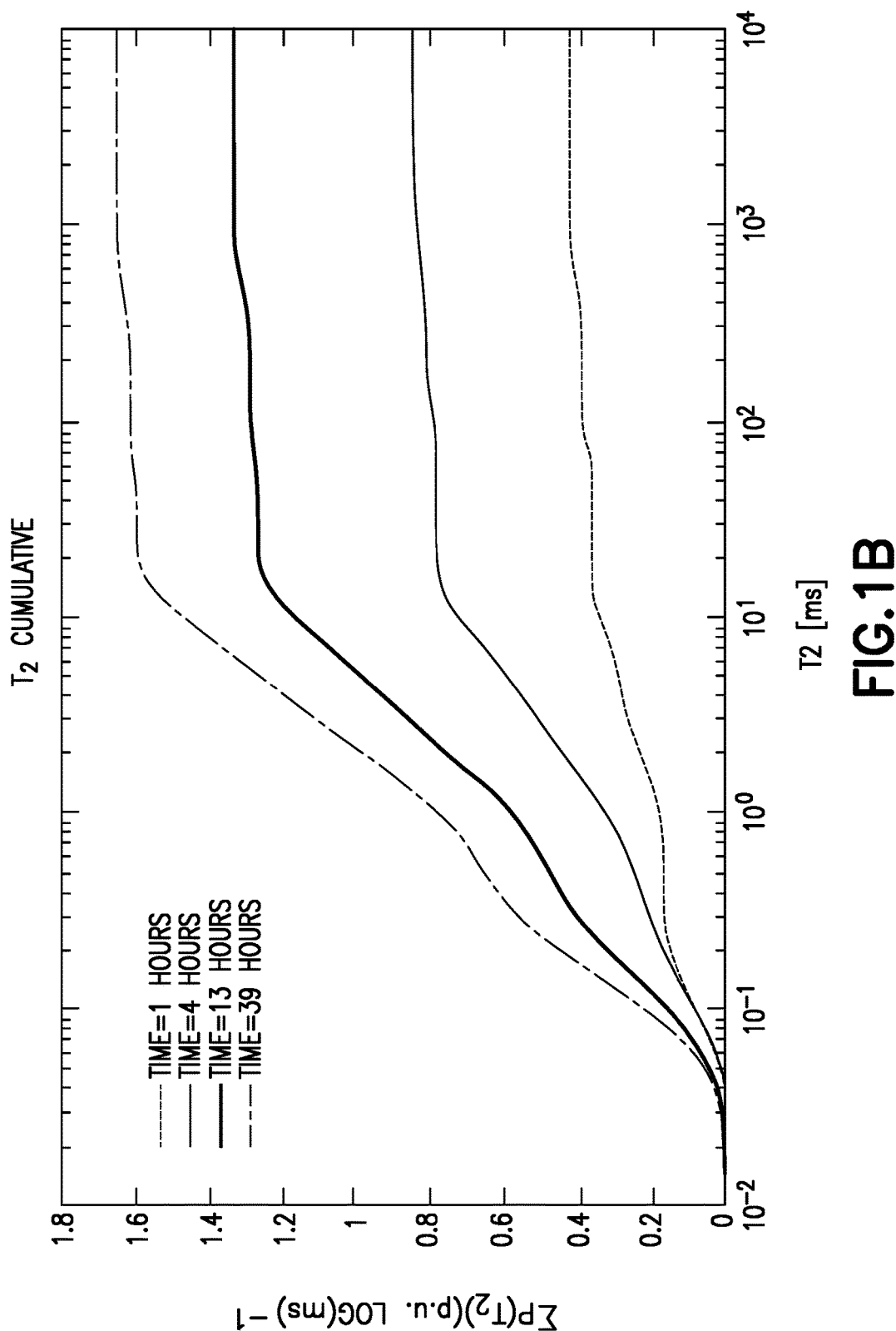
FIG. 1B is a plot showing the cumulative increase of the $T_2$ signal as gas is injected into the sample, in accordance with the present disclosure.
Figure 2:
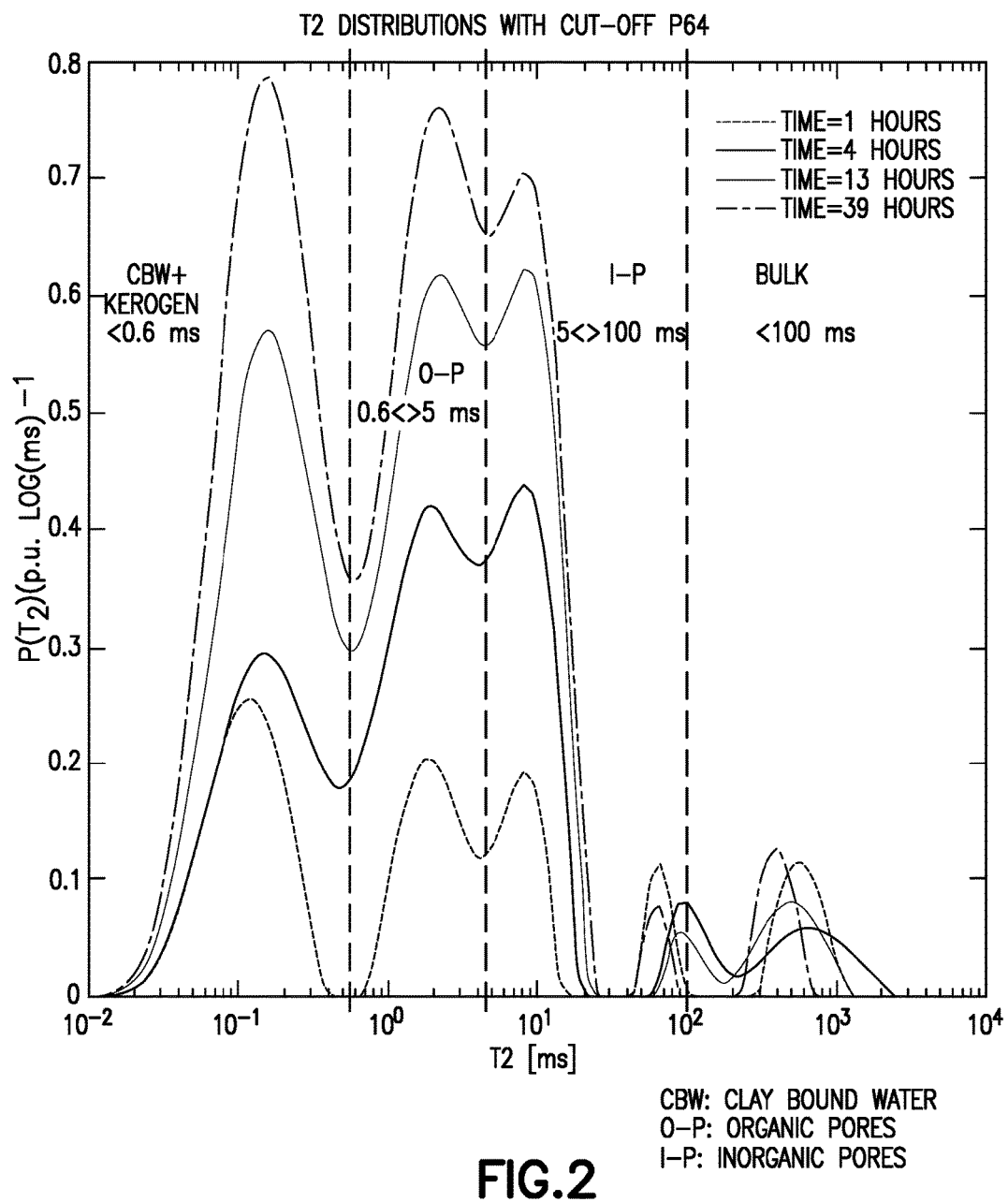
FIG. 2 is a plot of a $T_2$ distribution with a $T_2$ cutoff used to separate signal in different regions based on $T_2$ values, in accordance with the present disclosure.

The increase of the $T_2$ signal can be monitored as gas is injected into the sample, as shown in FIG. 1B. Similarly, the decrease of signal can be monitored as the sample is removed from the high gas pressure and left at ambient conditions. In this case, the gas will leave the sample, mimicking the gas production process from a gas reservoir. The different regions (i.e., pore regime or fluid state) can be differentiated based on their $T_2$ values using specific cutoff values. FIG. 2 shows the $T_2$ cutoff values required to separate the signal shown in FIG. 1. Using the cutoff values presented in FIG. 2, the regions can be distinguished and a plot of the amplitude of each component versus time can be extracted.

Figure 3B:
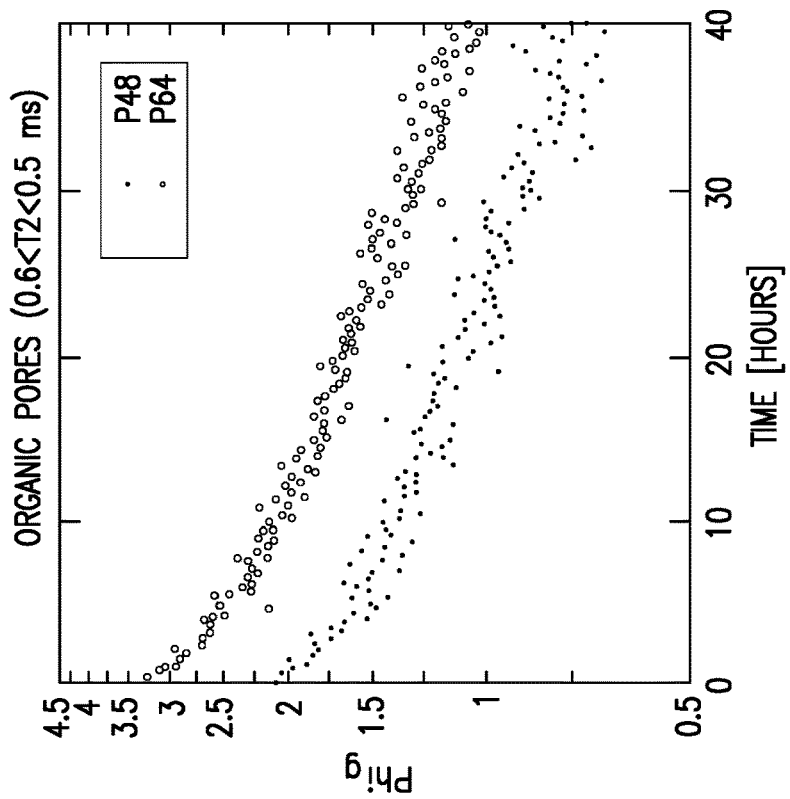
FIG. 3B is a plot of the amplitude of each of the $T_2$ components as a function of time for two different samples in the organic pores region, in accordance with the present disclosure.
Figure 3A:
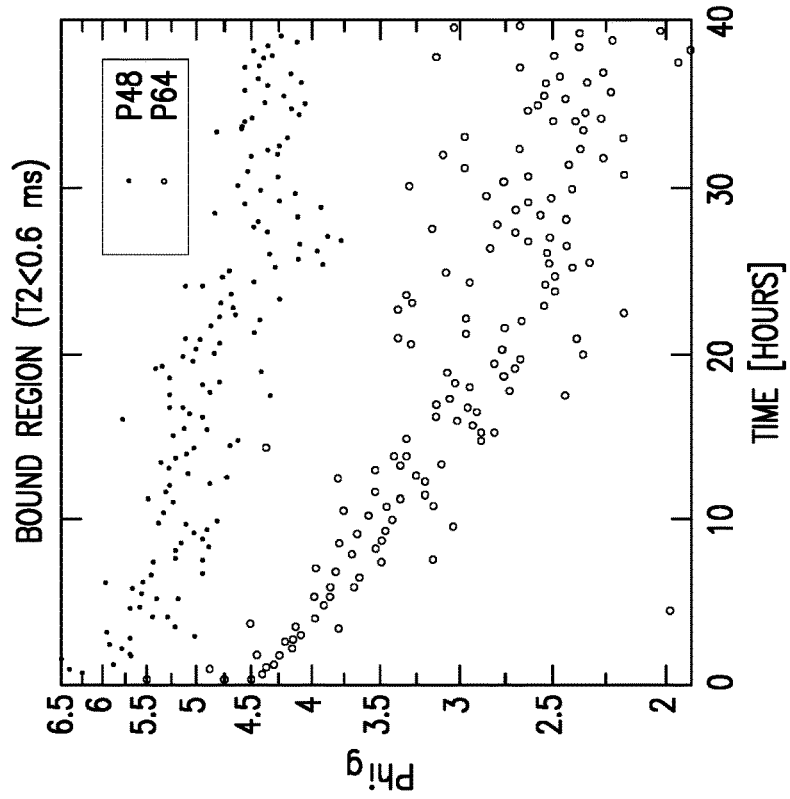
FIG. 3A is a plot of the amplitude of each of the $T_2$ components as a function of time for two different samples in the bound region, in accordance with the present disclosure.
Figure 3C:
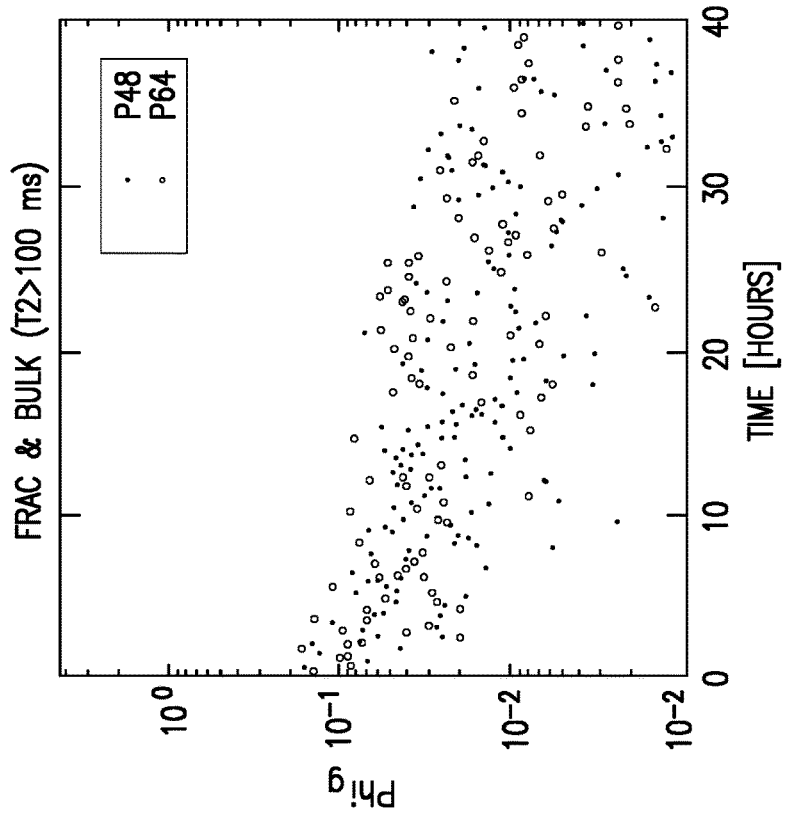
FIG. 3C is a plot of the amplitude of each of the $T_2$ components as a function of time for two different samples in the inorganic pores region, in accordance with the present disclosure.
Figure 3D:
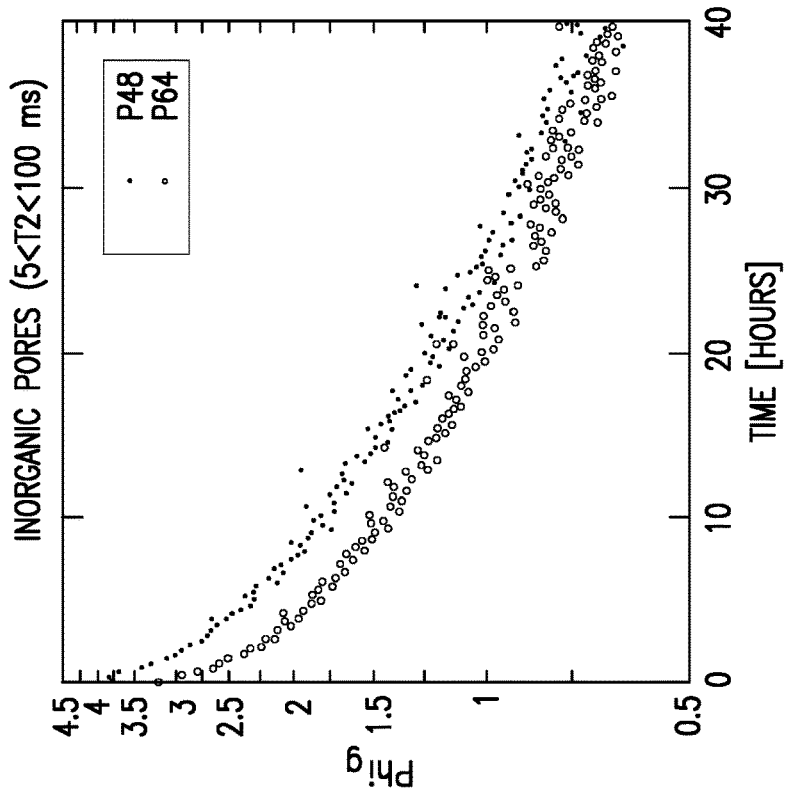
FIG. 3D is a plot of the amplitude of each of the $T_2$ components as a function of time for two different samples in the fracture and bulk region, in accordance with the present disclosure.

The behavior for each region for two different samples is presented in FIGS. 3A-3D. (Sample 2 is different from Sample 1, but is similar in lithology). FIG. 3A presents the "bound region", FIG. 3B presents the "organic pores" region, FIG. 3C presents the "inorganic pores" region, and FIG. 3D presents the "fracture and bulk" region. Note the regions occur over different time intervals of the $T_2$ distribution. This dataset intrinsically contains much more information than the simple (total) production as a function of time since it distinguishes production coming from different $T_2$ regions. The data in FIGS. 3A-3D correspond to the production stage after the gas pressure has been removed. Alternatively, an equivalent analysis can be done on the increasing signal as pressure is applied. Each of the decays in FIGS. 3A-3D can be fitted to extract the production rate for a specific region per sample.

Figure 4:
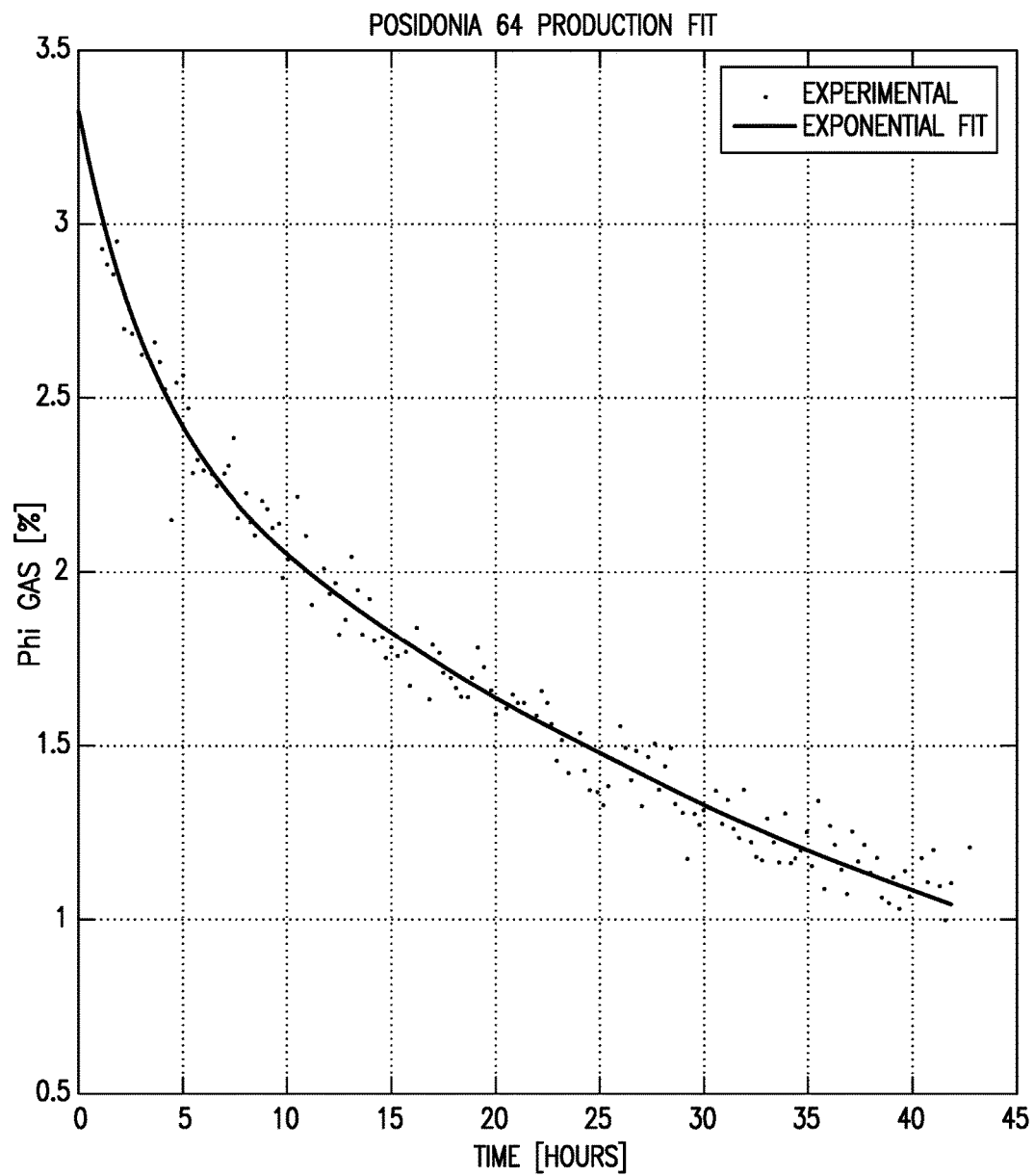
FIG. 4 is a plot of a bi-exponential fit to the organic pores (O-P, 0.6 ms<$T_2$<5 ms) part of the signal for Sample 1, in accordance with the present disclosure.

One possible fit for the organic pores component (FIG. 3B) of Sample 1 (P64) is shown in FIG. 4. In this case, the data were fitted accurately using a bi-exponential component. The fit to the pore volume over time can be used to infer fundamental properties of the sample that relate to parameters such as permeability, potential production rate, and overall production potential. A two-component fit is interpreted to include short-term behavior and long-term behavior of gas production that is coming from the same environment in the sample pore matrix.

In a further embodiment, applicable to laboratory studies, the core sample can be dried and weighed before injecting gas into the pore space. A micro-scale can be used to weigh the sample in situ while injecting gas and again while producing gas from the sample, without removing the sample from the NMR instrument. The weight of the sample increases as a result of gas injection in the pore space. Since the gas pressure is set by the user, it is already known. If the porosity of the rock is well characterized and inter-granular porosity and intra-kerogen porosity are known, then any convenient equation of state can be used along with these parameters to calculate the mass of gas injected into the pore space. This value may be compared with the measured weight gain as a result of gas injection into the sample. If the two values agree, the choice of equation of state and the porosity values are deemed reliable. In any event, the weight gain is a direct measure of total gas, although it may not be clear how the gas is partitioned within the different types of porosities (regions).

The gas may be allowed to escape (i.e., "produce") over time while the NMR and sample weight are monitored. The weight loss as a function of time provides an estimate of how much gas is produced over that time interval, while NMR measurements provide information regarding the type of porosity (region) from which this gas is coming. An NMR-based production curve can also be produced by integrating the area under each of the $T_2$ distribution curves as a function of time. This area is expected to decrease over time and the amount of this decrease can be used to calculate the amount of gas produced from each peak and/or the total peaks in each time interval.

Figure 5:
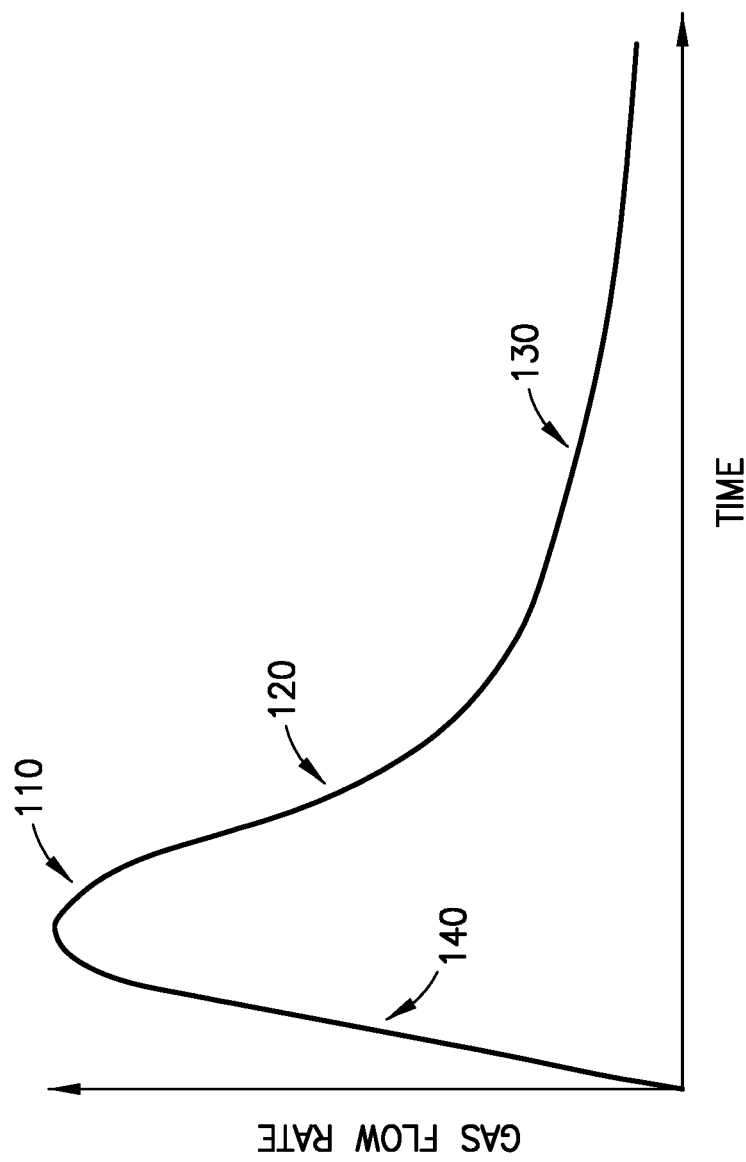
FIG. 5 is a plot of the gas flow rate as a function of time for an example production profile of a shale reservoir, in accordance with the present disclosure.

It is well known that the production profile from shale gas reservoirs resembles what is plotted in FIG. 5. As this figure shows, when the well is put in production, the initial gas flow rate 140 increases rather rapidly. In later times the increase slows down, leading to a peak 110. At later times the production begins to decrease according to decreasing flow rate 120, but in general does not decrease to zero. The long-term production profile of these wells is a smaller flow rate 130 that lasts several years.

Similar behavior is expected for core samples in the lab since the connection between the pore space and the well is by a fracture network that provides high permeability. For the laboratory experiments, the time-dependent weight gain simulates initial flow rate 140 while the initial decay simulates decreasing flow rate 120. At later times, when only small flow rate 130 is active, if the gas pressure is high enough to perform NMR measurements, these results provide detailed information about where the production associated with small flow rate 130 comes from. In any event, even if the pressure is below the sensitivity of an NMR instrument, the weight measurements are sensitive enough to trace a large portion of the decay according to small flow rate 130. The net result is a production profile similar to that shown in FIG. 5.

These profiles vary from one formation to another and are quite informative and helpful in production planning. In addition, these measurements comprising NMR data allow one to ascertain the type of porosity from which the gas is being produced and the volume of gas. Thus, the information obtained from investigating the core may be used to decide, for example, whether to put a well into production and the level of infrastructure needed for production.

Figure 6:
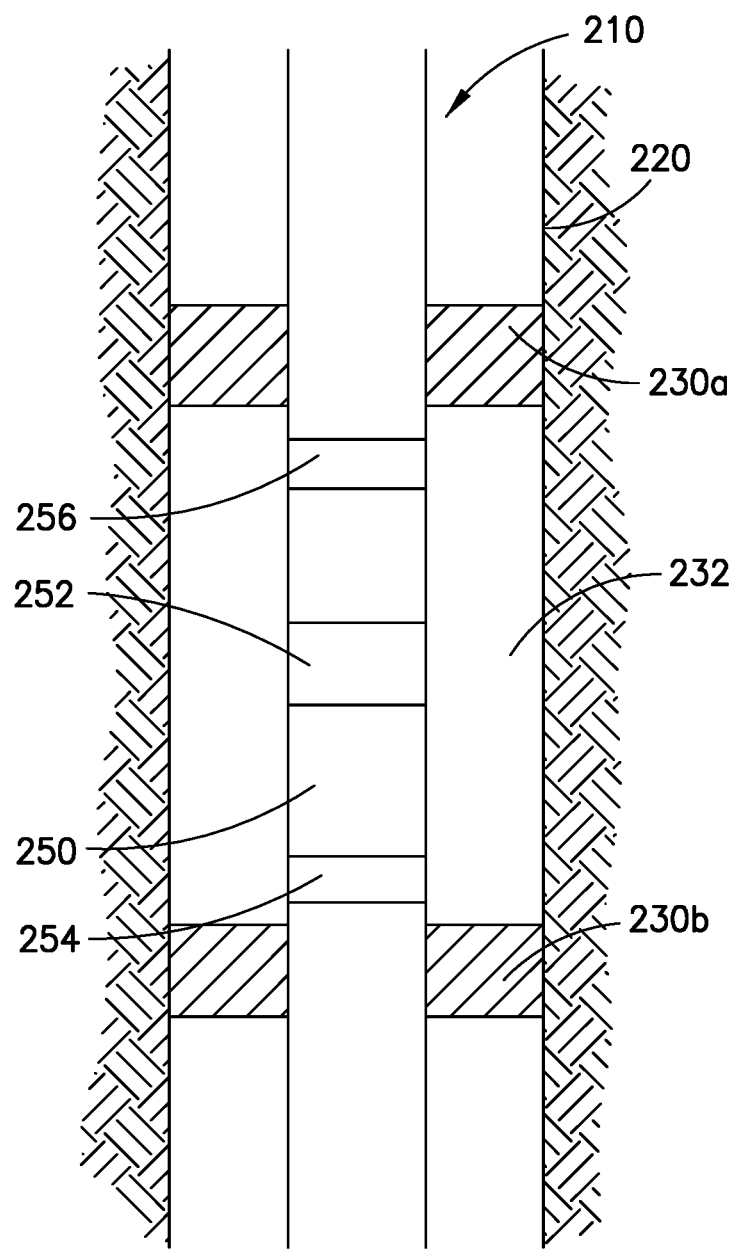
FIG. 6 is a schematic diagram of an NMR tool disposed in a wellbore, in accordance with the present disclosure.

In another embodiment, the NMR measurements are performed in situ downhole. FIG. 6 shows a well 210 drilled in a formation of interest. A logging tool 250 is lowered into the well 210 to the depth of interest. The logging tool 250 contains a pair of packers 230a and 230b that can be activated to make a hydraulic seal with the borehole wall 220 (as well as the tubular body of logging tool 250). This causes the space 232 to be hydraulically isolated from the remaining sections of the well, which contain drilling fluid. The logging tool 250 may also contain a pump-out unit 254 that is used to pump out the drilling fluid trapped in the isolated section 232. Once the space 232 is void of fluid, a pumping unit 256 is used to pump gas such as methane into the space 232 at pressures higher than or equal to the expected reservoir pressure.

Pumping continues until the pressure is stabilized, which can be established by monitoring the rate of pumped gas. At this point, the pump-out unit 254 may be used to remove any free gas in the space 232. An NMR instrument 252 that is part of the logging tool 250 may be used to make NMR measurements as a function of time, as described above, and the area under the $T_2$ distribution curves may be determined for each time interval. In one embodiment, the NMR tool has a depth of investigation that is larger than the borehole diameter and can be used to monitor the gas in the pore space, independent of the free gas in space 232. This allows for use while injecting the gas as well as while producing gas from the formation. As time increases, the NMR signal is expected to decrease in intensity and the incremental intensity (area) decrease can be calibrated or analytically related (e.g., using an equation of state) to the produced gas. The data may also be interpreted to determine the amount of gas in different pore types in the rock close to the borehole wall and the rate at which it can be produced. This information can be used, for example, to decide whether there is an economic incentive to complete and fracture the well.

Figure 7:
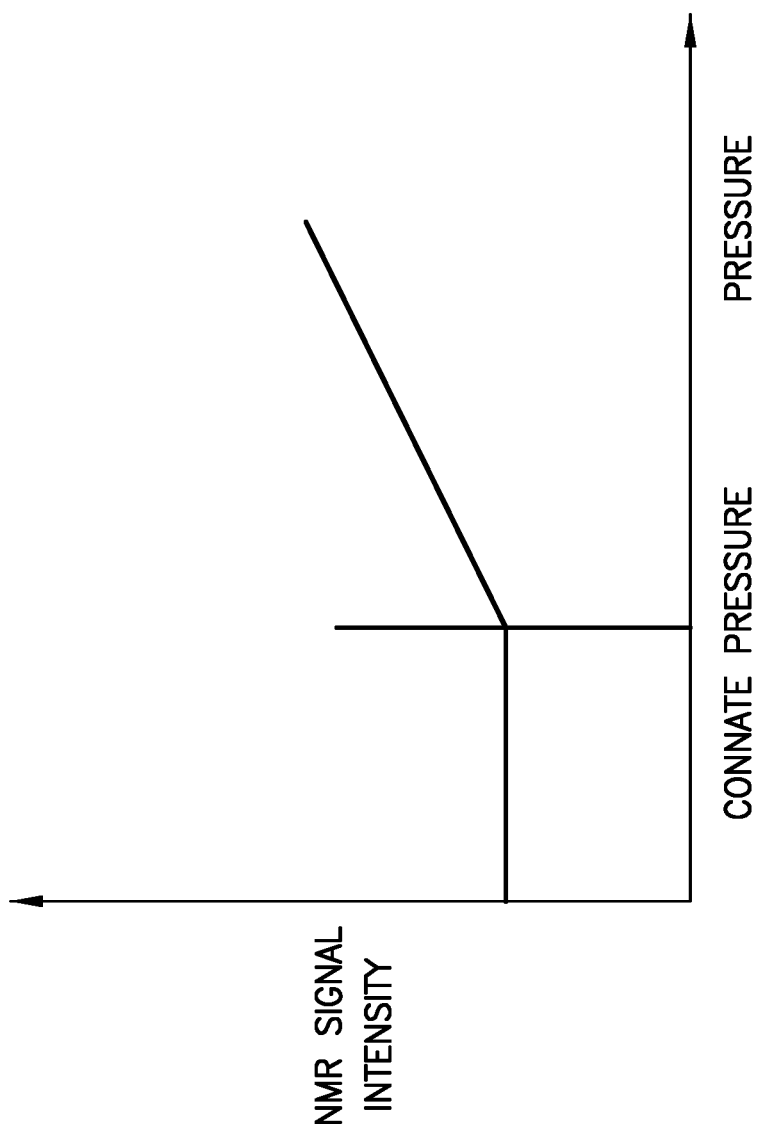
FIG. 7 is a plot of NMR signal intensity versus pressure, in accordance with the present disclosure.

Initially there is gas in the pore space that gives rise to the NMR signal. The pressure of this gas is a sought-after parameter and is not easily measurable. As new gas is injected, there will not be an NMR signal increase until the pressure of injected gas surpasses the connate gas pressure. This feature can be exploited to accurately estimate connate gas pressure to be, for example, the first pressure that causes NMR signal intensity to increase. If a plot of NMR signal intensity as a function of pressure is made, there will be a region of lower pressure where the injected gas has negligible effect on the NMR signal and a high pressure region where the signal increases with pressure. The latter can be extrapolated to the lowest pressure, which is the onset pressure causing NMR signal increase. This would be the connate gas pressure. A plot of NMR signal intensity versus pressure is shown in FIG. 7.

Figure 8:
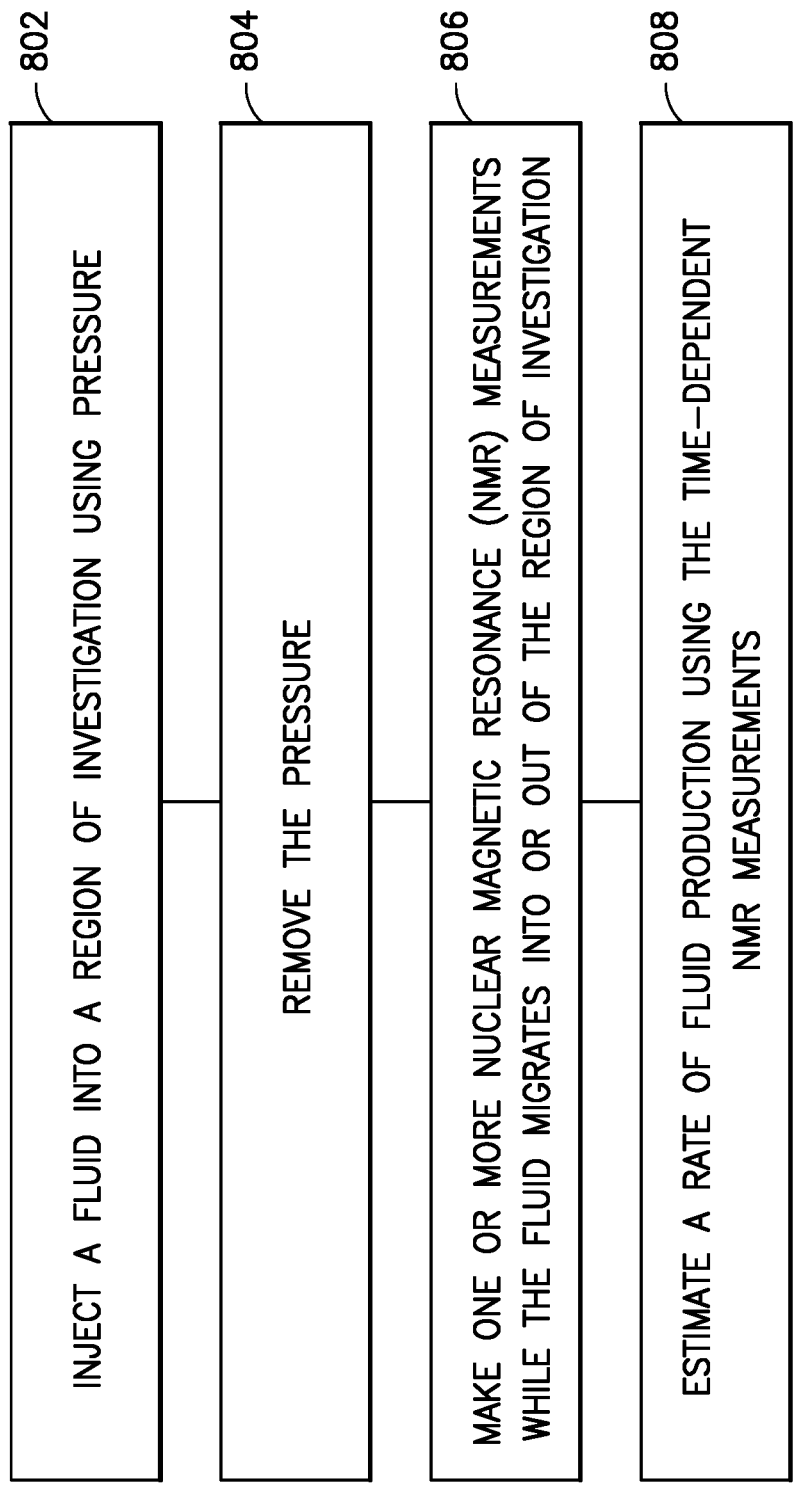
FIG. 8 is a workflow showing an embodiment using time-dependent NMR measurements to determine fluid production rates from different geologic reservoirs, in accordance with the present disclosure.

FIG. 8 is a flowchart for one embodiment using time-dependent NMR measurements to determine fluid production rates from different geologic reservoirs. A fluid is injected into a region of investigation using pressure (802). The pressure is removed (804) and one or more nuclear magnetic resonance (NMR) measurements while the fluid migrates into or out of the region of investigation is made (806). A rate of fluid production using the time-dependent NMR measurements is estimated (808).

The foregoing outlines features of several embodiments so that those skilled in the art may better understand the aspects of the present disclosure. Those skilled in the art should appreciate that they may readily use the present disclosure as a basis for designing or modifying other processes and structures for carrying out the same purposes and/or achieving the same advantages of the embodiments introduced herein. Those skilled in the art should also realize that such equivalent constructions do not depart from the scope of the present disclosure, and that they may make various changes, substitutions, and alterations herein without departing from the scope of the present disclosure.

The Abstract at the end of this disclosure is provided to comply with 37 C.F.R. § 1.72(b) to allow the reader to quickly ascertain the nature of the technical disclosure. It is submitted with the understanding that it will not be used to interpret or limit the scope or meaning of the claims.

While only certain embodiments have been set forth, alternatives and modifications will be apparent from the above description to those skilled in the art. These and other alternatives are considered equivalents and within the scope of this disclosure and the appended claims. Although only a few example embodiments have been described in detail above, those skilled in the art will readily appreciate that many modifications are possible in the example embodiments without materially departing from this invention. Accordingly, all such modifications are intended to be included within the scope of this disclosure as defined in the following claims. In the claims, means-plus-function clauses are intended to cover the structures described herein as performing the recited function and not only structural equivalents, but also equivalent structures. Thus, although a nail and a screw may not be structural equivalents in that a nail employs a cylindrical surface to secure wooden parts together, whereas a screw employs a helical surface, in the environment of fastening wooden parts, a nail and a screw may be equivalent structures. It is the express intention of the applicant not to invoke 35 U.S.C. § 112, paragraph 6 for any limitations of any of the claims herein, except for those in which the claim expressly uses the words 'means for' together with an associated function.

What is claimed is:

1. A method, comprising:
   injecting a fluid into a region of investigation using pressure;
   making one or more time-dependent nuclear magnetic resonance (NMR) measurements while the fluid migrates into the region of investigation under pressure;
   removing the pressure and making one or more time-dependent nuclear magnetic resonance (NMR) measurements while the fluid migrates out of the region of investigation; and
   estimating a rate of fluid production using the one or more time-dependent NMR measurements.

2. The method of claim 1, further comprising saturating the region of investigation with the fluid.

3. The method of claim 1, wherein the fluid is a gas, a liquid, or a supercritical fluid.

4. The method of claim 1, wherein the fluid is a hydrocarbon.

5. The method of claim 4, wherein the hydrocarbon is methane gas.

6. The method of claim 1, wherein the fluid is a proton-bearing fluid or a non-proton-bearing fluid having a spin-bearing target element.

7. The method of claim 1, wherein the fluid is a non-proton-bearing fluid having a spin-bearing target element selected from a group consisting of: $^{13}C$, $^{2}H$, $^{6}Li$, $^{10}B$, $^{11}B$, $^{14}N$, $^{15}N$, $^{17}O$, $^{19}F$, $^{23}Na$, $^{29}Si$, $^{31}P$, $^{35}Cl$, $^{113}Cd$, $^{129}Xe$, $^{195}Pt$.

8. The method of claim 1, wherein the region of investigation is an interior region in a core sample.

9. The method of claim 1, wherein the region of investigation is in situ in a formation, and further comprising hydraulically isolating a section of a wellbore proximate the region of investigation, and evacuating drilling fluid and/or wellbore fluid from the hydraulically isolated section of the wellbore.

10. The method of claim 9, wherein the formation is a shale.

11. The method of claim 1, wherein the one or more time-dependent NMR measurements are of a type selected from a group consisting of: a $T_2$ distribution, a $T_1$-$T_2$ distribution, and a diffusion distribution.

12. The method of claim 1, further comprising:
    discerning relative contributions from different pore systems or pore fluids based on the one or more time-dependent NMR measurements.

13. The method of claim 12, wherein the relative contributions are categorized as originating from a bound region, an organic pores region, an inorganic pores region, and a fracture and bulk region.

14. The method of claim 1, further comprising:
    interpreting multi-component decay for a single $T_2$ value or a single $T_2$ peak.

15. The method of claim 1, wherein the pressure is applied incrementally, removed incrementally, or applied and removed incrementally.

16. The method of claim 1, wherein the making one or more time-dependent NMR measurements comprises:
    making several NMR measurements at known times as the fluid enters the region of investigation or leaves the region of investigation.

17. The method of claim 1, wherein the making one or more time-dependent NMR measurements comprises making NMR measurements more closely spaced in time at the beginning of a saturation process and/or less closely spaced in time near the end of a de-saturation process.

18. The method of claim 1, further comprising:
inferring properties of the region of investigation based on a curve fitting to NMR response over time.

19. The method of claim 18, wherein the properties include one or more of: permeability, potential production rate, and overall production potential.

20. The method of claim 1, further comprising:
determining an NMR signal response as a function of pressure, and
estimating a connate gas pressure using the determined NMR signal response as a function of pressure.

21. A method, comprising:
measuring the mass of a dried sample having a pore space;
injecting a fluid into the sample pore space using pressure, thereby producing an injected sample;
measuring the mass of the injected sample;
removing the pressure;
measuring the mass of the injected sample as a function of time as the fluid migrates out of the sample pore space;
determining the change in mass of the injected sample as a function of time as the fluid migrates out of the sample pore space; and
estimating a rate of fluid production using the determined change in mass as a function of time.

22. The method of claim 21, further comprising:
making one or more nuclear magnetic resonance (NMR) measurements while the fluid migrates into or out of the sample pore space, and
estimating a rate of fluid production using the time-dependent NMR measurements.

23. The method of claim 22, further comprising:
comparing the estimated rate of fluid production using the determined change in mass as a function of time to the estimated rate of fluid production using the time-dependent NMR measurements.

* * * * *